United States Patent [19]
Terada

[11] 3,962,917
[45] June 15, 1976

[54] RESPIROMETER HAVING THERMOSENSITIVE ELEMENTS ON BOTH SIDES OF A HOT WIRE

[75] Inventor: Hideshi Terada, Takatsuki, Japan

[73] Assignee: Minato Medical Science Co., Ltd., Osaka, Japan

[22] Filed: July 3, 1974

[21] Appl. No.: 485,537

[52] U.S. Cl. ............................. 73/204; 128/2.08
[51] Int. Cl.² ..................... G01F 1/68; A61B 5/08
[58] Field of Search ............ 73/189, 204; 128/2.08

[56] References Cited
UNITED STATES PATENTS

| | | | |
|---|---|---|---|
| 2,728,225 | 12/1955 | Skibitzke | 73/204 |
| 3,060,723 | 10/1962 | Kapff et al. | 73/204 X |
| 3,075,515 | 1/1963 | Richards | 73/204 X |
| 3,081,766 | 3/1963 | Dubsky et al. | 128/2.08 |
| 3,592,055 | 7/1971 | Dorman | 73/204 X |
| 3,648,518 | 3/1972 | Hans et al. | 73/204 |
| 3,680,378 | 8/1972 | Aurilio et al. | 128/2.08 X |
| 3,687,130 | 8/1972 | McCormick | 128/2.08 |

*Primary Examiner*—Herbert Goldstein
*Attorney, Agent, or Firm*—Flynn & Frishauf

[57] ABSTRACT

A respirometer for measuring the rate of an air flow of respiration includes a hot wire in a path of the air flow. For measuring the rate of the air flow with a discrimination made between the senses of the air flow, a pair of temperature sensitive elements are placed in the path of the air flow on respective opposite sides of the hot wire relative to the air flow.

10 Claims, 6 Drawing Figures

RESPIROMETER HAVING THERMOSENSITIVE ELEMENTS ON BOTH SIDES OF A HOT WIRE

BACKGROUND OF THE INVENTION

This invention relates to a respirometer of the hot resistance wire anemometer type.

A conventional respirometer of the type described is useful in measuring the rate of an air flow of respiration of an animal, which may be a human being. This is because the respirometer gives little resistance to the air flow and has a small volume which would otherwise adversely affect the measurement as a serious dead void. It has been heretofore mandatory when measuring the rate of the air flow with a discrimination made between expiration and inspiration to use the conventional respirometer with a unidirectional valve attached thereto for allowing passage of the air flow of either expiration or inspiration only. It is to be mentioned here that the discrimination between expiration and inspiration is equivalent to a discrimination between the senses of the air flow. Returning back to the subject, use of the prior unidirectional valve makes it impossible to continually observe the respiration.

SUMMARY OF THE INVENTION

It is therefore an object of the present invention to provide a respirometer of hot resistance wire anemometer type, capable of measuring the rate of an air flow of respiration with a discrimination made between the senses of the air flow.

It is another object of this invention to provide a respirometer of the type described, capable of further continually measuring the quantity of the air flow of respiration.

A respirometer of the type described includes a hot wire disposed in a path of the air flow. In accordance with this invention, the respirometer comprises a pair of thermosensitive or temperature sensitive elements in the path of the air flow on both sides of the hot wire.

It is to be noted in connection with the gist of this invention set forth above that a "hot wire" as denoted herein means a resistance wire, such as a wire used in the hot resistance wire anemometer, through which an electric current may be caused to flow to raise the temperature of the wire to a predetermined temperature range. The "hot wire" may be provided separately from the counterpart of a hot resistance wire used in the anemometer as will later become clear. In this case, the hot resistance wire and an accompanying measuring electrical circuit serve as means for producing an electric output signal representative of the rate of the air flow, but without a discrimination being made between the senses of the air flow. When the "hot wire" is used also as the counterpart of the hot resistance wire, means may accompany the hot wire for producing the electric output signal representative of the rate of the air flow without the discrimination being made.

Figure 1:
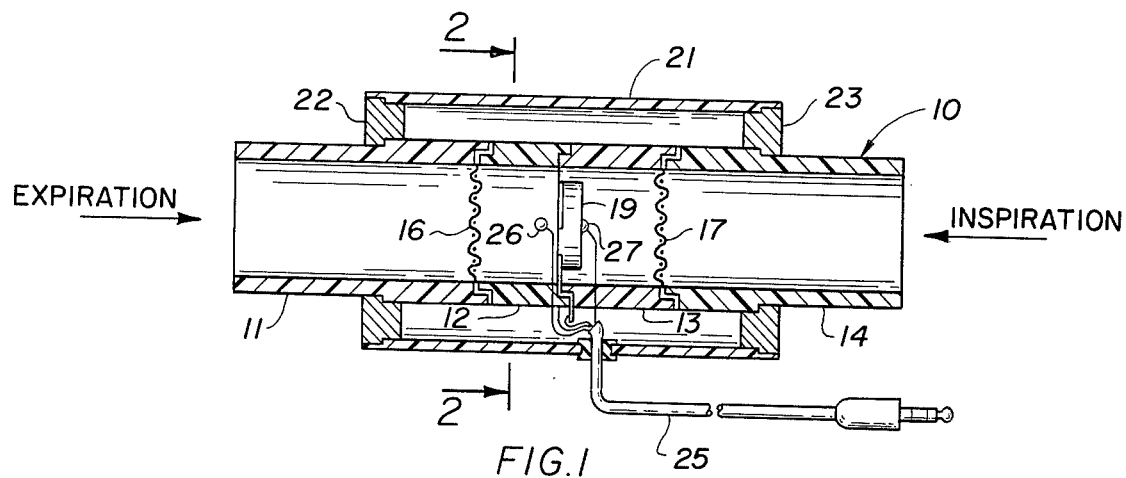
FIG. 1 is a schematic axial sectional view of a respirometer unit according to a first embodiment of the instant invention.
Figure 2:
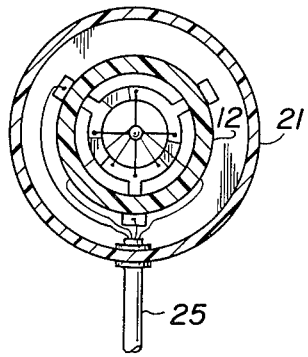
FIG. 2 is a schematic cross-sectional view of the respirometer unit taken on a plane represented in FIG. 1 by a line 2—2.
Figure 3:
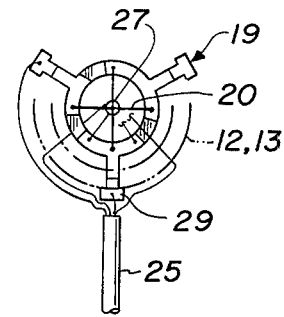
FIG. 3 schematically shows a hot wire of the respirometer unit together with a temperature sensitive element disposed at the back thereof and related elements.

DESCRIPTION OF THE PREFERRED EMBODIMENTS:

Referring to FIGS. 1 through 3, a transducer or respirometer unit 10 comprises a plurality of cylindrical tubes 11, 12, 13, and 14, a first and a second fine mesh 16 and 17, and a hot wire holder 19 for a hot wire 20. Preferably, the tubes 11 through 14 have a common inside diameter, such as 20 mm, and are made of an electrically insulating material which may be a plastic material. The meshes 16 and 17 may be made of fine stainless steel wires. The hot wire 20 may be made of platinum, tungsten, any other metal, or a semiconductor material. In the example being illustrated, the hot wire holder 19 comprises a ring member of an electrically insulating material having an outside diameter smaller than the common inside diameter of the tubes 11 through 14 and three conductor pieces attached to the ring member as best shown in FIG. 3. Each conductor piece has a leg that extends beyond the outside surfaces of the tubes 12 and 13 when the holder 19 is interposed between and concentrically of these tubes 12 and 13 in the manner depicted in FIG. 1. Also, a pair of hot wires 20 are attached to the conductor pieces in a crosswise configuration with a small gap, which may be about 1 mm, left therebetween. The respirometer unit 10 further comprises an outer tube 21 and a pair of annular members 22 and 23 for integrally uniting in combination the inner tubes 11 through 14 with the meshes 16 and 17 and the hot wire holder 19 interposed as best shown in FIG. 1. The inner tubes 11 through 14 thus cooperate to form a path of an air flow of respiration, in which path the meshes 16 and 17 and the hot wire or wires 20 are placed. The first and second meshes 16 and 17 serve as filters for the air flow of expiration and inspiration, respectively. The conductor piece legs serve to hold the hot wire holder 19 in place. The outer tube 21 may be made of a plastic material while the annular members 22 and 23 may be made of aluminium, although these elements 21 through 23 may be made of any other materials. The meshes 16 and 17 may be equally or unequally spaced from the hot wire 20. The distance may be about 10 to 20 mm. For example, the first mesh 16 placed upstream of the hot wire 20 with respect to the air flow of expiration is spaced about 20 mm from the hot wire 20 while the second mesh 17 is spaced about 10 mm therefrom. The respirometer unit 10 still further comprises a multi-conductor cord 25. Two of the cord conductors have free ends electrically connected to two of the hot wire holder conductor piece legs so as to enable an electric current to flow through the hot wire 20 to raise the temperature to a predetermined temperature range. The temperature for a platinum hot wire may be about 400°C while that for a tungsten hot wire may be about 150°C.

Further referring to FIGS. 1 through 3, the respirometer unit 10 according to a first embodiment of the present invention comprises a first and a second thermosensitive or temperature sensitive element 26 and 27 in the path of the air flow of respiration on both sides of the hot wire or wires 20. Each of the elements 26 and 27 may be a platinum or tungsten wire, several microns in diameter, or a resistance wire of any other metal whose electric resistivity is dependent on the temperature. Alternatively, the elements 26 and 27 may be made of a semiconductor material or be thermocouples. A wire may either be extended like the hot wire 20 or bent into a hairpin shape. In FIGS. 1 through 3, the elements 26 and 27 are shown as thermistors. Inasmuch as the hot wire holder 19 shown there has the hot wire 20 on its upstream end with respect to the air flow of expiration, the second thermistor 27 is depicted as put halfway into the hollow space enclosed with the holder 19. Preferably, the elements 26 and 27 have small heat capacity and are placed diametrically centrally of the path of air flow, spaced about 1 to 2 mm from the hot wire or wires 20. One end of each temperature sensitive element 26 or 27 is electrically connected to that predetermined one 29 of the hot wire holder conductor pieces or their legs as best illustrated in FIG. 3, to which one end of the hot wire or wires 20 is also connected. The cord 25 here comprises four conductors. The other ends of the temperature sensitive elements 26 and 27 are electrically connected to free ends of the two remaining cord conductors.

In operation, the air flow of expiration successively passes through the first mesh 16, the first temperature sensitive element 26, the hot wire 20, the second temperature sensitive element 27, and the second mesh 17. While passing through the hot wire 20, the exhaled air is heated to raise the temperature of the second temperature sensitive element 27 higher than that of the first temperature sensitive element 26. On the contrary, the air flow of inspiration renders the temperature of the first element 26 higher than that of the second element 27. The temperature of the inhaled air is substantially equal to the ambient temperature and the temperature of the exhaled air is approximately equal to the bodily temperature of the animal concerned. As described, the temperature of the hot wire 20 is appreciably higher than these temperatures of the air. This makes it possible to continually measure the rate and quantity of respiration as will later be detailed with a discrimination made between the senses of the air flow. In practice, the temperature of the elements 26 and 27 is kept somewhat higher than the ambient temperature while the elements 26 and 27 are not subjected to the air flow of respiration. Although not yet precisely determined, the actual temperature rise in the element 26 or 27 disposed downstream of the hot wire 20 with respect to the air flow is presumably of the order of 80° to 90°C. In any event, it has been confirmed that the respirometer according to this invention works well. The temperature of the hot wire 20 is kept substantially constant throughout the measurement. In other words, the respirometer is of a constant temperature type.

Figure 4:
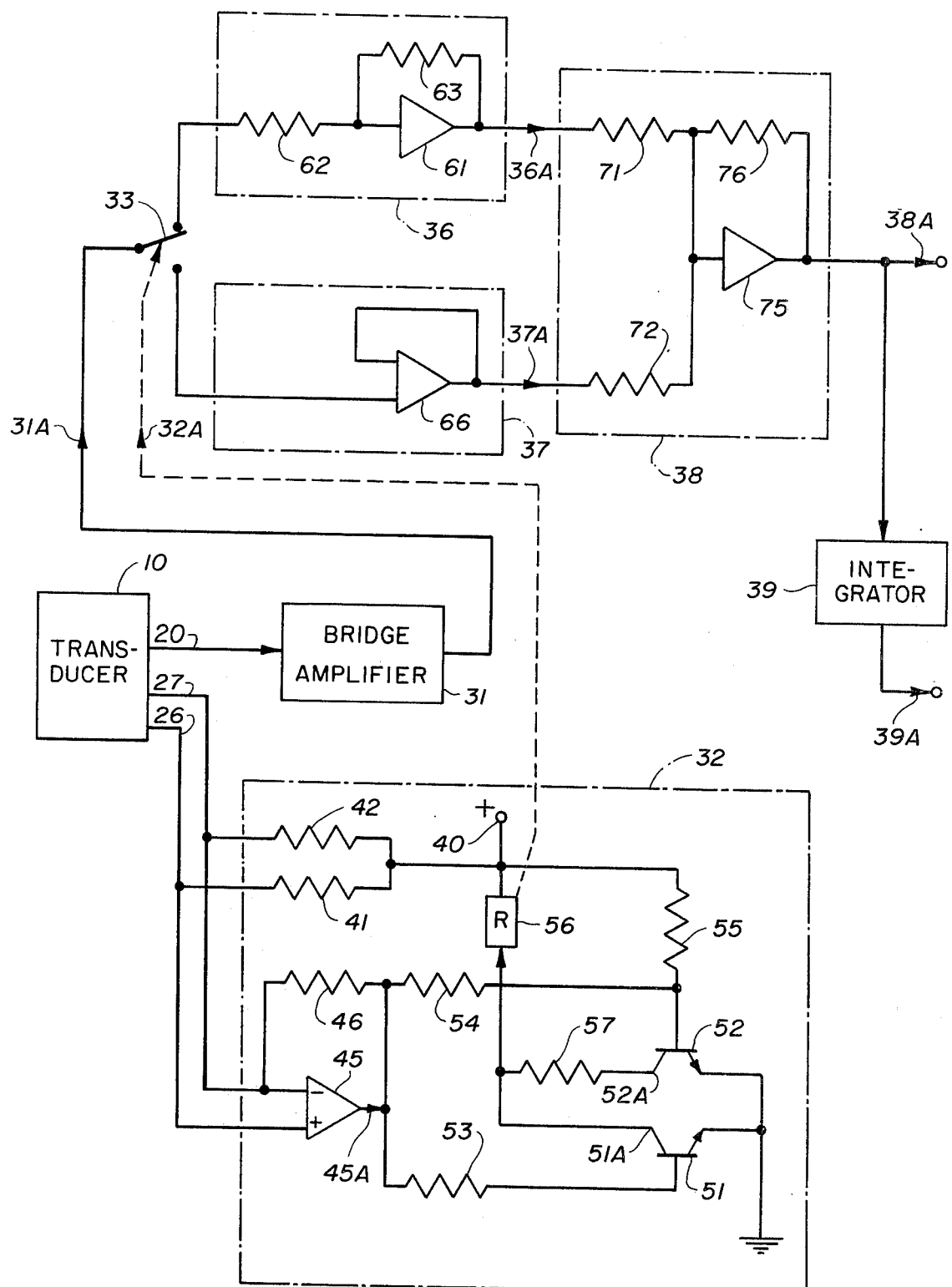
FIG. 4 is a diagram of a respirometer circuit, partly shown in blocks, for use in combination with the respirometer unit.
Figure 5:
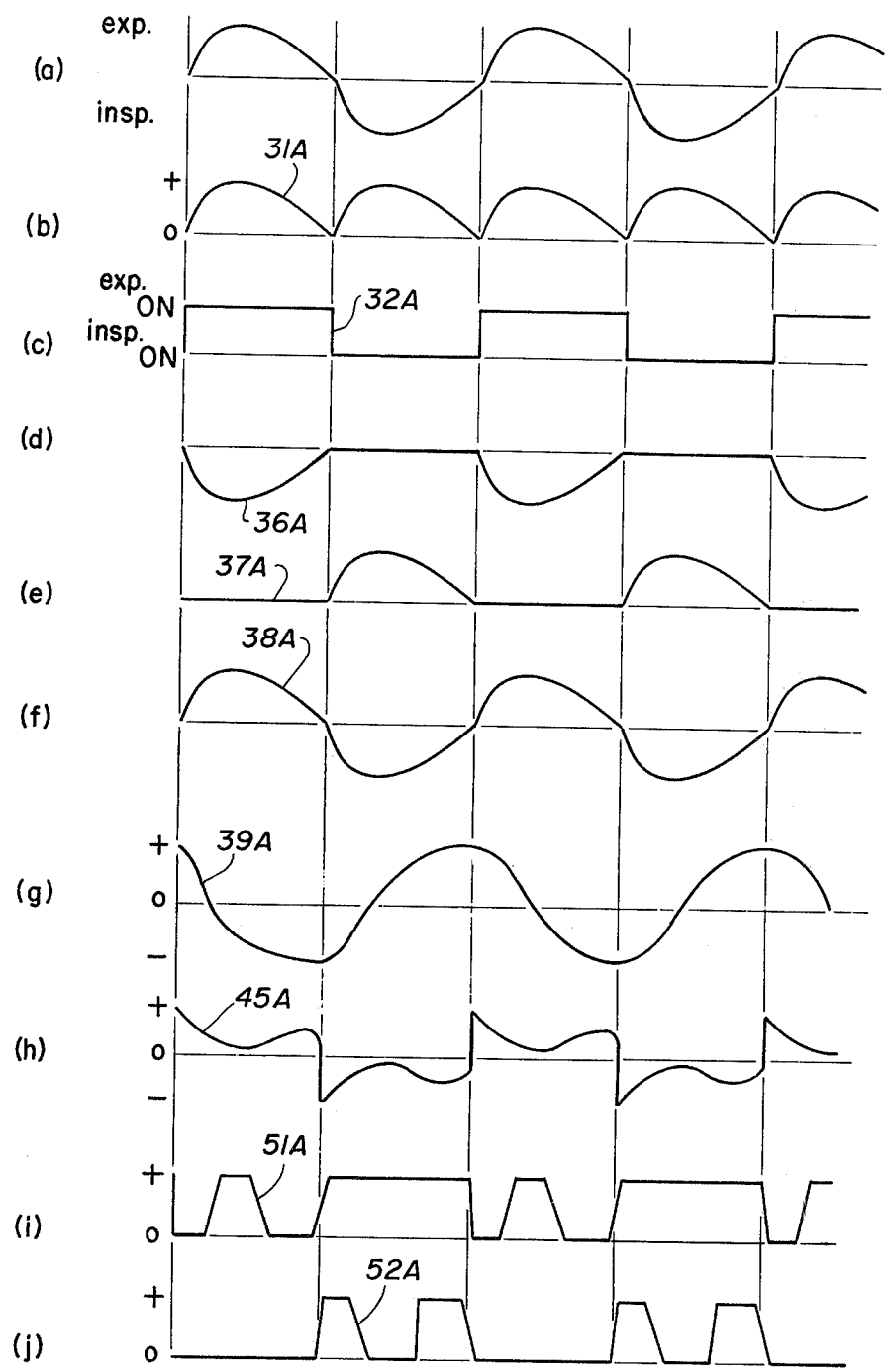
FIG. 5 primarily shows signals derived at several points of the respirometer circuit.

Referring additionally to FIGS. 4 and 5, a respirometer circuit for use in combination with the respirometer unit 10 illustrated with reference to FIGS. 1 through 3 comprises a conventional hot wire bridge amplifier 31 electrically connected to the hot wire 20 through the cord 25 for producing an electric output signal representative of the rate of respiration, namely, the quantity of the air flowing per unit time through the respirometer unit 10 as a result of respiration. As described, the bridge amplifier 31 should be capable of supplying a variable electric current to the hot wire 20 to keep the temperature thereof substantially constant despite the cooling effected thereon by the air flow of respiration and of producing an electric output signal by measuring the variation in the electric current. Such a bridge amplifier 31 may be obtained from Minato Medical Science Co., Ltd., Osaka, Japan. In any event, the bridge amplifier 31 produces an electric output signal 31A representative of the rate of respiration without a discrimination made between the senses of the air flow. The actual rate of respiration as measured by a pneumotachograph is depicted in FIG. 5 (a). As described in the preamble of the instant specification, it is impossible to discriminate between expiration and inspiration merely with an electric output signal 31A which the bridge amplifier 31 produces as shown in FIG. 5 (b). In accordance with this invention, the respirometer circuit comprises a sense discrimination circuit 32 responsive to the electric resistances of the temperature sensitive elements 26 and 27 for effecting control in the manner later described and symbolized at 32A in FIG. 5 (c) on relay contacts 33, which supplies the bridge amplifier output signal 31A to a selected one of a first or expiration and a second or inspiration amplifier 36 and 37 for producing a first or expiration and a second or inspiration rate signal 36A and 37A in the manner also later described and depicted in FIGS. 5 (d) and (e). The circuit further comprises a combining amplifier 38 responsive to the rate signals 36A and 37A for producing a respiration rate signal 38A in the manner later described and illustrated in FIG. 5 (f). The circuit yet further comprises an integrator 39 for integrating the respiration rate signal 38A to produce a respiration quantity signal illustrated in FIG. 5 (g).

Referring specifically to FIG. 4 and again to FIG. 5, the sense discrimination circuit 32 comprises a power source 40, a pair of bias resistors 41 and 42 for supplying background electric currents to the temperature sensitive elements 26 and 27 from the power source 40, and a differential amplifier 45 responsive to the electric resistances of the elements 26 and 27 and accompanied by a resistor 46 for adjusting the amplification. If thermistors are used as the elements 26 and 27 as described, the resistance of the first element 26 becomes generally higher and lower than that of the second element 27 during expiration and inspiration, respectively. It follows therefore, roughly speaking, that the differential amplifier 45 produces a differential output signal 45A which becomes positive and negative during expiration and inspiration, respectively. More particularly, the differential output signal 45A is definitely positive at the beginning of expiration as illustrated in FIG. 5 (h) and decreases substantially to zero as the rate of expiration increases to reduce the temperature difference between the elements 26 and 27. As the rate of expiration decreases at the end of the expiration period, the differential output signal 45A again becomes positive. When inspiration begins, the differential output signal 45A becomes to negative. Similar changes occur in the differential output signal 45A during the inspiration period and subsequently following respiration periods. The sense discrimination circuit 32 further comprises a first and a second transistor 51 and 52 whose base electrodes are supplied with the differential output signal 45A through resistors 53 and 54 and connected to the power source 40 through the resistors 53 and 54 and a common resistor 55 and through the common resistor 55 only, respectively. The emitter electrodes of the transistors 51 and 52 are grounded. A relay 56 is connected between the power source 40 and the collector electrodes of the first and second transistors 51 and 52 directly and through a holding resistor 57, respectively. The first transistor 51 is thus turned on when the differential output signal 45A becomes positive as shown in FIG. 5 (*i*) by its collector potential 51A. The second transistor 52 is also conductive at this time as depicted in FIG. 5 (*j*) by its collector potential 52A. At this moment, the relay 56 is energized to switch by the control 32A the relay contacts 33 to the expiration amplifier 36 as shown in FIG. 4. When the differential output signal 45A decreases toward zero during expiration, the first transistor 51 is turned off as seen from FIG. 5(*i*). The relay 56, however, remains energized by the electric current flowing through the holding resistor 57 and the second transistor 52. The energization of relay 56 continues substantially throughout expiration even when the differential output signal 45A again becomes more positive at the end of expiration. When the differential output signal 45A becomes negative at the beginning of the following inspiration period, the first transistor 51 is turned off. The second transistor 52 is also turned off because the electric current flowing into its base electrode through the common resistor 55 now flows instead to the output terminal of the differential amplifier 45 through the resistor 54. The relay 56 is therefore deenergized to switch the relay contacts 33 by the control 32A to the inspiration amplifier 37. When the differential output signal 45A increases toward zero, the second transistor 52 is turned off. The holding resistor 57, however, prevents the relay 56 from being energized. Thus, the transistor circuit 32 produces a control signal that assumes a first and a second value during the expiration and inspiration periods, respectively.

Further referring to FIGS. 4 and 5, the expiration amplifier 36 comprises a differential amplifier 61 and a series and a parallel resistor 62 and 63 for adjusting the amplification substantially to minus unity. The expiration rate signal 36A consequently appears only during the expiration periods and is an inverted bridge amplifier output signal. The inspiration amplifier 37 comprises a differential amplifier 66 whose output terminal is connected directly to one of its input terminals so as to render the amplification substantially equal to plus unity. The inspiration rate signal 37A therefore appears solely during the inspiration periods and is a reproduction of the bridge amplifier output signal. The combining circuit 38 comprises a pair of resistors 71 and 72 for summing up the expiration and inspiration rate signals 36A and 37A, a differential amplifier 75 supplied with the sum, and a resistor 76 interposed between the input and output terminals of the differential amplifier 75 to adjust the amplification thereof.

It will now readily by understood that the relay contacts 33 may supply the bridge amplifier output signal 31A to the first and second amplifiers 36 and 37 during the expiration and inspiration periods, respectively. It will also be appreciated that the relay 56 and the amplifiers 36 through 38 cooperate to operate on (or) modify the electric output signal 31A only when the control signal assumes one of the first and second values and that the respirometer according to this invention produces the respiration rate signal 38A representative of the rate of respiration with a discrimination made between expiration and inspiration and the respiration quantity signal 39A representative of the quantity or volume of air inhaled by the animal concerned, a negative quantity representing the quantity of air exhaled by the animal.

Figure 6:
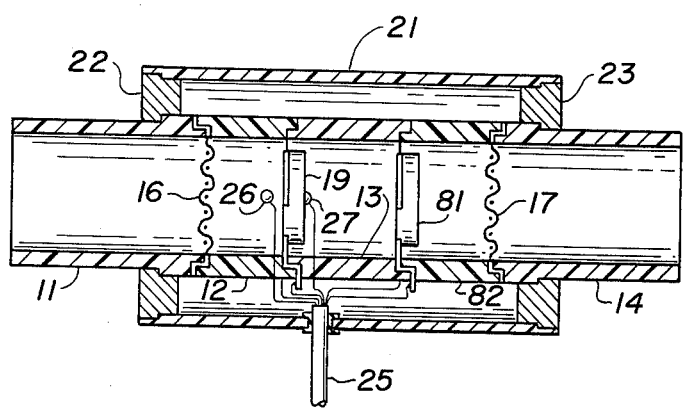
FIG. 6 is a schematic axial sectional view of a respirometer unit according to a second embodiment of this invention.

Referring finally to FIG. 6, a respirometer unit according to a second embodiment of this invention comprises similar elements designated with like reference numerals as in the unit 10 according to the first embodiment. The unit according to the second embodiment comprises in addition another holder 81 for a hot resistance wire (not shown) on one side of a combination of the "hot wire" and the temperature sensitive elements 26 and 27 for specifically measuring the rate of respiration without the discrimination of the expiration and inspiration and an additional inner tube 82 for facilitating the assembly of the unit. The unit according to the second embodiment is suitable when the power supplied to the hot resistance wire held by the additional holder 81 for measurement of the rate of respiration is insufficient to properly operate the temperature sensitive elements 26 and 27, which are now operated by the "hot wire" held by the first holder 19 and used merely as a heater.

What is claimed is:

1. A respirometer for use in measuring the rate of an air flow of respiration, comprising:
   means for defining a one-dimensional path of air flow of respiration;
   a hot wire in said respiration air flow path;
   means coupled to said hot wire for maintaining said hot wire substantially at a predetermined temperature;
   a pair of temperature sensitive elements in said respiration air flow path on respective opposite sides of said hot wire relative to the air flow of respiration in said air flow path, said temperature sensitive elements having an electrical characteristic which varies as a function of temperature;
   first means electrically connected to said hot wire for producing an electrical output signal representative of the rate of said air flow but without discriminating between the senses of the direction of said air flow; and
   second means electrically connected to said first means and to said temperature sensitive elements, said second means including:
      third means electrically connected to said temperature sensitive elements for producing a control signal that assumes a first value during expiration and a second value during inspiration; and
      fourth means electrically connected to said first and third means and including: switching means responsive to said control signal; first electrical operating means coupled to said switching means and having a first electrical characteristic for operating on said electrical output signal of said first means during inspiration for providing an inspiration output signal; second electrical operating means coupled to said switching means and having a second electrical characteristic for operating on said electrical output signal of said first means during expiration for providing an expiration output signal, and combining means coupled to said first and second electrical operating means for combining the inspiration and expiration output signals thereof and producing a respiration rate signal representative of the rate of said air flow with discrimination between the senses of the direction of said air flow.

2. A respirometer as claimed in claim 1, wherein each of said temperature sensitive elements is spaced about 1 millimeter from said hot wire on said respective opposite sides of said hot wire.

3. A respirometer as claim in claim 1, further comprising a hot resistance wire in said air flow path on one side of a combination of said hot wire and temperature sensitive elements.

4. A respirometer as claimed in claim 3, further comprising means electrically connected to said hot resistance wire for producing an electrical output signal representative of the rate of said air flow but without discriminating between the senses of the direction of said air flow.

5. A respirometer as claimed in claim 1, wherein said means for maintaining the temperature of said hot wire substantially at said predetermined temperature includes means electrically connected to said hot wire for supplying a variable electric current to said hot wire.

6. A respirometer as claimed in claim 1, further comprising an integrator connected to said second means for integrating said respiration rate signal to produce a respiration quantity signal representative of the quantity of said air flow.

7. A respirometer as claimed in claim 1, wherein said third means comprises differential amplifier means connected to said temperature sensitive elements for producing a differential output signal that assumes substantially positive and negative values during one and the other of expiration and inspiration periods of respiration, respectively, and a transistor circuit responsive to said differential output signal for producing said control signal of said first and second values when said differential output signal assumes said positive and negative values, respectively.

8. A respirometer as claimed in claim 1 wherein said first electrical operating means comprises a first amplifier, said second electrical operating means comprises a second amplifier and said combining means comprises means for summing the electrical output signals from said first and second amplifiers.

9. A respirometer as claimed in claim 1 wherein said switching means includes a relay operable in response to said control signal for switching said electrical output signal of said first means between said first and second electrical operating means.

10. A respirometer for use in measuring the rate of an air flow of respiration, comprising:
means for defining a one-dimensional path of air flow of respiration;
a hot wire in said respiration air flow path;
means coupled to said hot wire for maintaining said hot wire substantially at a predetermined temperature;
a pair of temperature sensitive elements in said respiration air flow path on respective opposite sides of said hot wire relative to the air flow of respiration in said air flow path, said temperature sensitive elements having an electrical characteristic which varies as a function of temperature;
first means electrically connected to said hot wire for producing an electrical output signal representative of the rate of said air flow but without discriminating between the senses of the direction of said air flow; and
second means electrically connected to said first means and to said temperature sensitive elements, and responsive to said electrical output signal of said first means and to said electrical characteristics of said temperature sensitive elements for producing a respiration rate signal representative of the rate of said air flow with discrimination between the senses of the direction of said air flow, said second means including:
third means electrically connected to said temperature sensitive elements for producing a control signal that assumes a first value during expiration and a second value during inspiration; and
fourth means electrically connected to said first and third means, said fourth means comprising a first amplifier means for producing a first output signal with an amplification substantially equal to minus unity, a second amplifier means for producing a second output signal with an amplification substantially equal to plus unity, a combining circuit coupled to said first and second amplifier means and reponsive to said first and second output signals from said first and second amplifier means for producing a combined output signal, and relay means electrically connected to said first and third means and operative responsive to said control signal from said third means for supplying said electrical output signal from said first means to said first amplifier means when said control signal assumes one of said first and second values, and for supplying said electrical output signal from said first means to said second amplifier means when said control signal assumes the other of said first and second values, said combined signal thereby becoming said respiration rate signal.

* * * * *